United States Patent [19]

Gould, III

[11] 4,449,982

[45] May 22, 1984

[54] PROJECTILE

[75] Inventor: Jay W. Gould, III, Bloomington, Minn.

[73] Assignee: Minnesota Mining and Manufacturing Company, Saint Paul, Minn.

[21] Appl. No.: 965,102

[22] Filed: Nov. 30, 1978

Related U.S. Application Data

[63] Continuation of Ser. No. 740,663, Nov. 10, 1976, abandoned.

[51] Int. Cl.$^3$ .............................................. A61M 5/00

[52] U.S. Cl. .................................. 604/891; 102/512; 273/428; 604/49

[58] Field of Search ............... 273/106 R, 106 E, 428; 102/92, 92.7, 92.1, 502, 512; 128/260; 119/1; 604/891, 49

[56] References Cited

U.S. PATENT DOCUMENTS

| | | | |
|---|---|---|---|
| Re. 12,927 | 3/1909 | Gleinich | 102/92.1 |
| 2,982,550 | 5/1961 | Francis | 273/106 E |
| 3,948,263 | 4/1976 | Drake, Jr. et al. | 102/92 X |
| 3,982,536 | 9/1976 | Krogseng et al. | 102/92 X |

*Primary Examiner*—Paul E. Shapiro

*Attorney, Agent, or Firm*—Donald M. Sell; James A. Smith; William L. Huebsch

[57] ABSTRACT

A projectile adapted to be propelled at sub-sonic speeds to carry a dose of medicament or an electronic device into an animal while causing minimum physical damage to the animal's hide or flesh. The projectile has an average density of less than about 5 grams per cubic centimeter, an elongate body portion adapted for close fitting engagement in a barrel from which the projectile is propelled, and a conical nose portion having a radiused apex. A method of implanting a medicament or device in the flesh of an animal. The medicament or device is combined in the projectile and the projectile is propelled nose first at sub-sonic speed from a range of one to sixty feet through the hide of the animal so that the nose portion causes only a slit in the hide of the animal, which is shorter than the diameter of the projectile, and so that the projectile makes only limited penetration of the flesh.

2 Claims, 4 Drawing Figures

PROJECTILE

This is a continuation of application Ser. No. 740,663 filed Nov. 10, 1976, now abandoned.

BACKGROUND OF THE INVENTION

This invention relates to projectiles adapted to be ballistically implanted into animals.

The art is replete with projectiles or bullets designed to be fired into animals with a view to disabling or killing the animal. Typically such projectiles have a high average density of about 10 grams per cubic centimeter, and are designed for deep penetration of animal flesh and for delivering great shocking power which causes maximum trauma to the animal.

SUMMARY OF THE INVENTION

In contrast, the projectile according to the present invention when propelled at sub-sonic speeds will cleanly enter the animal without causing significant damage to the animal's hide or flesh. Also the projectile will come to rest within the animal's flesh within a relatively short distance from the point of entry irrespective of the distance from which the projectile is propelled toward the animal within a range of from about 1 to 60 feet ($\frac{1}{3}$ to 18 meters). If the projectile strikes a bone or semi-rigid member within the animal, it will be stopped or deflected without significant damage to the bone or member.

According to the present invention there is provided a projectile having an elongate body portion with a central axis adapted for close fitting engagement with the inner surface of the bore of a barrel from which the projectile is propelled (e.g. such as the barrel of a compressed gas powered device) and a generally conical nose portion coaxial with the body portion. The conical nose portion has a base diameter corresponding generally in cross sectional area to the cross sectional area of the body portion, and a small radius on its apex.

The projectile according to the present invention is adapted for safely carrying a medicament (e.g. a vaccine, antibiotic or worming compound) or a device (e.g. such as an electronic locating or marking device as is described in U.S. patent application Ser. No's. 504,057 and 504,060) into the flesh of an animal. The body and nose portions of the projectile could be entirely formed of a uniform mixture of medicament and binder. Alternatively the projectile may be formed of soluble or insoluble rigid low density material and define a central cavity communicating with the end of the body portion opposite the nose portion in which cavity a medicament or a device may be carried. Preferably, such a cavity has a cylindrical portion which is coaxially located within the body portion of the projectile and has a hemispherical front portion at its end adjacent the nose portion. The hemispherical portion of the cavity smoothly joins the cylindrical portion, thereby eliminating any corners in the cavity, which, if they were present, could cause stress concentration points and resultant shearing between portions of the projectile upon impact.

The body portion must have a diameter sufficient to afford a cavity which can contain a dose of medicament or a device of a significant size, and yet should be as small as possible to minimize the wound that it causes. Body portions of from 0.177 to 0.30 inch in diameter are most suitable with body portions of 0.25 inch in diameter being preferred. For some limited applications of shallow implantation, body portions of up to 0.45 inch may also be suitable.

The projectile is preferably formed of a low density material (i.e. having an average density of no greater than 5 grams per cubic centimeter and preferably less than 2 grams per cubic centimeter) to limit its striking power, such that with a medicament in the cavity, the average density of the combined projectile and medicament is less than 2 grams per cubic centimeter, and even with an electronic device in the cavity the average density of the combined projectile and device is less than 5 grams per cubic centimeter. When it is used for delivering a medicament to animals raised for human consumption, the projectile is preferably formed of a rigid material adapted to be assimilated into the animal, such as from equal parts by weight of calcium carbonate and the hydroxypropyl cellulose sold under the trade designation "Klucel" and available from Hercules, Inc.

It has been found that to afford clean effective limited penetration into an animal of such a low density projectile propelled at sub-sonic speed, the nose portion of the projectile should be conical in shape with an apex angle of over 45 degrees and up to 75 degrees (with an angle of 60 being preferred), and should have an apex or terminal end surface which is radiused at a dimension of from 0.015 to 0.020 inch. Low density projectiles with hemispherical or parabolically rounded nose portions tend to punch holes in the hide of an animal into which they are propelled at sub-sonic velocities and can thus carry a portion of hide into the wound which provides a source of infection. Also such projectiles upon entering the flesh of an animal will cause substantial trauma and resulting hematoma such that a large welt can immediately be seen to rise on the animal after the projectile enters. Low density projectiles with a conical nose portion having an apex angle in the indicated range, but with a pointed instead of a radiused apex tend to stick into but not penetrate the hide of an animal when propelled against the animal at sub-sonic speeds. Surprisingly, however, projectiles with both the conical nose portion and the radiused apex of the shapes indicated will easily penetrate the hide of an animal and cause only minimal damage to the animal flesh. Penetration by such a projectile causes only a slit in the hide where it enters. This entry slit has a shorter length dimension than the diameter of the projectile, and little if any bleeding occurs through the slit. The projectile does not carry a portion of the animal's hide into the wound. Also such a projectile moves through the flesh without causing significant trauma and resulting hematoma so that only a relatively small welt is raised in the area where the projectile enters. Additionally such a projectile seems to penetrate only a limited distance into the flesh of the animal (i.e. 2 to 5 inches depending on the age of the animal) irrespective of the distance to the animal from which the projectile is propelled in the range of between about 1 to 60 feet.

Preferably the projectile has a concave surface at its end opposite the nose portion which concave surface may be provided by the body portion or by a medicament or a device in the cavity. The concave surface produces much greater accuracy of flight for the projectile than does a flat end, presumably because it restricts tipping forces at the edge of the projectile due to escaping gas as the projectile exits from a barrel, and is particularly useful in obtaining accuracy for uniform mass projectiles.

BRIEF DESCRIPTION OF THE DRAWING

The present invention will be further described with reference to the attached drawing wherein like numbers refer to like parts in the several views, and wherein.

DESCRIPTION OF THE PREFERRED EMBODIMENT

Figure 2:
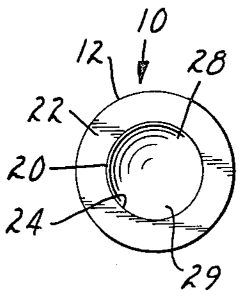
FIG. 2 is an end view of the projectile of FIG. 1.
Figure 1:
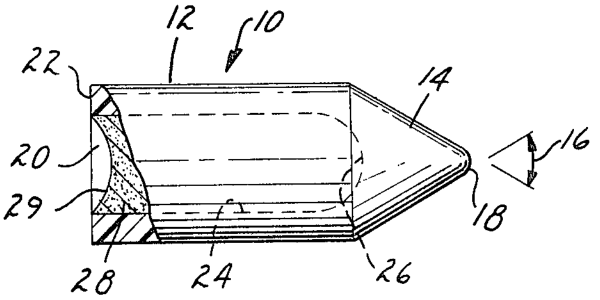
FIG. 1 is a side view partially in section of a first embodiment of a projectile according to the present invention illustrated with a medicament in a chamber formed therein.

Referring now to the drawing, there is shown in FIGS. 1 and 2 a projectile according to the present invention generally designated by the numeral 10. The projectile 10 comprises an elongate body portion 12 having a central axis and a cylindrical outer surface 0.25 inch in diameter. The body portion 12 is adapted to fit closely into the inner surface of a barrel from which the projectile is propelled as by being deformed into rifling in the barrel. Also the projectile includes a conical tip portion 14 coaxial with the body portion 12. The base of the tip portion 14 corresponds generally in cross sectional area with the cross sectional area of the body portion 12. The conical tip portion 14 has an apex angle 16 of 60 degrees and has a 0.016 inch radius on its apex or terminal end surface 18, the center of which radius is on the axis of the tip portion 14.

The projectile 10 has a cavity 20 opening through the end surface 22 of the projectile 10 opposite the tip portion 14 which cavity 20 is defined by a cylindrical inner surface 24 smoothly joined at its end opposite the end surface 22 with a hemispherical surface 26 so that no stress concentration points are provided within the projectile 10. As illustrated, the cavity 20 is filled with a medicament 28 such as in the form of a compacted or freeze dried powder, which medicament 28 is shaped to provide a concave surface portion 29 at the end surface 22 of the projectile 10. The edge of the concave surface portion 29 is shown at the end surface 22 of the projectile but could be recessed within the cavity 20.

Figure 4:
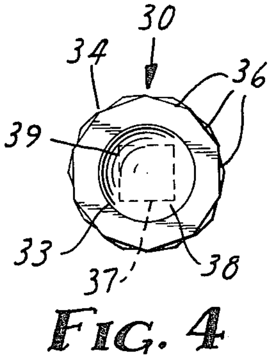
FIG. 4 is an end view of the projectile of FIG. 3.
Figure 3:
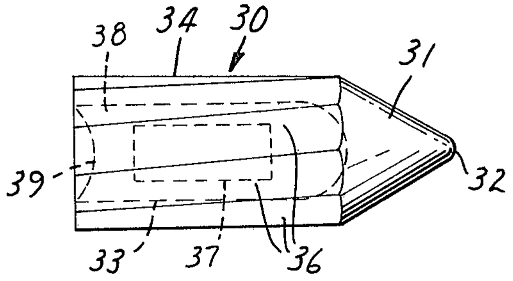
FIG. 3 is a side view of a second embodiment of a projectile according to the present invention illustrated with an electronic device secured in a chamber formed therein.

FIGS. 3 and 4 illustrate an alternate embodiment of a projectile according to the present invention generally designated by the numeral 30. Like the projectile 10 of FIGS. 1 and 2, the projectile 30 has a conical tip portion 31 with a base generally corresponding in cross sectional area with the cross sectional area of an elongate body portion 34, a radiused apex or tip surface 32, and a cavity 33 which are respectively shaped like the tip portion 14, tip surface 18 and cavity 20 of the projectile 10. The body portion 34 of the projectile 30, however, is not cylindrical on its outer surface. Instead it has ten flatted surface portions 36 of equal width around its periphery, which flatted surface portions 36 are evenly twisted about the axis of the projectile 30. These flatted surface portions 36 are adapted to fit closely within mating twisted flatted surfaces on the inner surface of a barrel from which the projectile 30 is to be propelled to provide a desired rotation during flight of the projectile. Also instead of a medicament, the cavity 33 contains a device 37 secured in place by an epoxy resin 38, which device may be adapted to be electronically activated to locate an animal carrying the projectile. The resin 18 securing the device in place provides a concave end surface 39 for the projectile 30.

I claim:

1. A method of implanting a medicament or device in the flesh of an animal comprising the steps of:

combining the medicament or device in a projectile having an average density of no greater than 5 grams per cubic centimeter, an elongated body portion with a diameter between 0.177 and 0.30 inch and a central axis, and a generally conical nose portion coaxial with and projecting from one end of said body portion, said nose portion having a base corresponding generally in cross sectional area with the adjacent cross sectional area of said body portion, an apex angle of greater than 45 degrees and up to 75 degrees, and having a 0.015 to 0.02 inch radius on its apex; and propelling the projectile nose portion first at subsonic speeds through the hide and into the flesh of the animal so that the nose portion causes only a slit in the hide of the animal where the projectile enters which slit is shorter in length than the diameter of the projectile, and the projectile will make limited penetration of the flesh of the animal with limited damage thereto.

2. A method according to claim 1, wherein said step of propelling is done from a range of between 1 to 60 feet.

* * * * *